(12) United States Patent
Lawrence

(10) Patent No.: US 8,307,531 B2
(45) Date of Patent: Nov. 13, 2012

(54) APPARATUS AND METHOD OF MANUFACTURING BODILY FLUID TEST STRIP

(75) Inventor: Gregory M. Lawrence, Indianapolis, IN (US)

(73) Assignee: Polymer Technology Systems, Inc., Indianapolis, IN (US)

( * ) Notice: Subject to any disclaimer, the term of this patent is extended or adjusted under 35 U.S.C. 154(b) by 331 days.

(21) Appl. No.: 12/772,707

(22) Filed: May 3, 2010

(65) Prior Publication Data

US 2010/0205797 A1     Aug. 19, 2010

Related U.S. Application Data

(62) Division of application No. 11/206,590, filed on Aug. 17, 2005, now abandoned.

(60) Provisional application No. 60/602,210, filed on Aug. 17, 2004.

(51) Int. Cl.
*B23P 25/00* (2006.01)

(52) U.S. Cl. .............. 29/458; 29/527.1; 72/333; 83/55; 422/400; 422/430; 435/4; 435/287.1

(58) Field of Classification Search ............... 29/458, 29/527.1, 896.6; 422/400, 401, 407, 421, 422/426, 430; 435/4, 11, 287.1, 287.8, 287.9; 72/333, 338; 83/55
See application file for complete search history.

(56) References Cited

U.S. PATENT DOCUMENTS

| | | | |
|---|---|---|---|
| 3,809,617 A | * | 5/1974 | Schmitt ...................... 435/287.7 |
| 4,178,153 A | | 12/1979 | Sodickson |
| 4,319,008 A | | 3/1982 | Marze et al. |
| 4,362,078 A | * | 12/1982 | Ohnishi et al. .................. 83/862 |
| 4,477,575 A | | 10/1984 | Vogel et al. |
| 4,738,823 A | | 4/1988 | Engelmann |
| 4,774,192 A | | 9/1988 | Terminiello et al. |

(Continued)

FOREIGN PATENT DOCUMENTS

DE          3217925 A1     11/1983

(Continued)

OTHER PUBLICATIONS

In the US Patent and Trademark Office U.S. Appl. No. 10/962,272, Non-Final Office Action dated Mar. 5, 2007, 8 pages; response dated Jun. 5, 2007, 35 pages; and additional response dated Jun. 5, 2007, 10 pages.

(Continued)

*Primary Examiner* — David Bryant
*Assistant Examiner* — Christopher Koehler
(74) *Attorney, Agent, or Firm* — Patton Boggs LLP

(57) ABSTRACT

There is a dry test strip holder having a test port and a retainer defining a well about the test port, and a sheet of test strip material. A test element that is 50% or less greater than the size of the test port is cut from the sheet using a die and punch. The punch drives the test element through a channel in the die while the cone-shaped outer surface of the die spreads the retainer, allowing the test element to drop into the well. A cap is snapped over the retainer to capture the test element.

12 Claims, 7 Drawing Sheets

U.S. PATENT DOCUMENTS

| | | | |
|---|---|---|---|
| 4,780,411 A | 10/1988 | Piejko et al. | |
| 4,916,056 A | 4/1990 | Brown, III et al. | |
| 4,943,522 A | 7/1990 | Eisinger et al. | |
| 4,987,085 A | 1/1991 | Allen et al. | |
| 5,013,339 A | 5/1991 | Mahoney et al. | |
| 5,104,619 A * | 4/1992 | de Castro et al. | 422/422 |
| 5,135,716 A | 8/1992 | Thakore | |
| 5,145,583 A | 9/1992 | Angleraud et al. | |
| 5,166,051 A * | 11/1992 | Killeen et al. | 435/7.1 |
| 5,212,060 A | 5/1993 | Maddox | |
| 5,240,862 A | 8/1993 | Koenhen et al. | |
| 5,389,338 A * | 2/1995 | Fish | 422/401 |
| 5,580,744 A | 12/1996 | Zweig | |
| 5,597,532 A * | 1/1997 | Connolly | 422/401 |
| 5,676,032 A * | 10/1997 | Johnson | 83/697 |
| 5,695,947 A | 12/1997 | Guo et al. | |
| 5,753,497 A | 5/1998 | Bernstein et al. | |
| 5,888,827 A | 3/1999 | Kayahara et al. | |
| 6,008,059 A | 12/1999 | Schrier et al. | |
| 6,040,195 A * | 3/2000 | Carroll et al. | 436/514 |
| 6,063,337 A | 5/2000 | Markart | |
| 6,130,100 A * | 10/2000 | Jobling et al. | 436/518 |
| 6,162,397 A * | 12/2000 | Jurik et al. | 422/423 |
| 6,171,849 B1 | 1/2001 | Rittersdorf et al. | |
| 6,194,164 B1 | 2/2001 | Matsui et al. | |
| 6,287,867 B1 | 9/2001 | Harttig et al. | |
| 6,342,364 B1 | 1/2002 | Watanabe et al. | |
| 6,440,306 B1 | 8/2002 | Ditter et al. | |
| 6,488,828 B1 | 12/2002 | Bhullar et al. | |
| 6,699,720 B1 * | 3/2004 | Lee et al. | 436/91 |
| 6,759,190 B2 | 7/2004 | Lin et al. | |
| 6,939,468 B2 | 9/2005 | Wang et al. | |
| 7,135,150 B2 | 11/2006 | Noda | |
| 2001/0005488 A1 | 6/2001 | Hirao et al. | |
| 2002/0043095 A1* | 4/2002 | Mason et al. | 73/1.02 |
| 2003/0003522 A1 | 1/2003 | Goldman | |
| 2003/0092102 A1 | 5/2003 | Rosen et al. | |
| 2003/0143523 A1* | 7/2003 | Kato et al. | 435/4 |
| 2003/0166291 A1 | 9/2003 | Jones et al. | |
| 2003/0175153 A1* | 9/2003 | Anaokar et al. | 422/56 |
| 2004/0126830 A1 | 7/2004 | Shull et al. | |
| 2004/0167237 A1 | 8/2004 | Kim et al. | |
| 2005/0003523 A1* | 1/2005 | Anaokar et al. | 435/287.2 |
| 2005/0170447 A1 | 8/2005 | Lawrence et al. | |
| 2006/0062688 A1 | 3/2006 | Lawrence | |
| 2006/0188392 A1 | 8/2006 | Tanaka et al. | |

FOREIGN PATENT DOCUMENTS

| | | |
|---|---|---|
| DE | 3401932 A1 | 8/1985 |
| DE | 19942928 A1 | 4/2001 |
| EP | 0260965 A | 3/1988 |
| EP | 0269876 A | 6/1988 |
| EP | 0389003 A | 9/1990 |
| EP | 0418169 A | 3/1991 |
| EP | 0511120 A | 10/1992 |
| EP | 0597268 A | 5/1994 |
| EP | 0753583 A | 1/1997 |
| JP | 02064455 | 3/1990 |
| WO | WO-00/73797 A | 12/2000 |
| WO | WO-03/025574 A | 3/2003 |
| WO | WO-03/058252 A2 | 7/2003 |

OTHER PUBLICATIONS

In the US Patent and Trademark Office U.S. Appl. No. 10/962,272, Final Office Action dated Aug. 17, 2007, 8 pages; and response dated Nov. 16, 2007, 5 pages, including Request for Continued Examination.

In the US Patent and Trademark Office U.S. Appl. No. 10/962,272, Non-Final Office Action dated Feb. 25, 2008, 6 pages; and response dated Mar. 18, 2008, 8 pages.

In the US Patent and Trademark Office U.S. Appl. No. 11/206,590, Non-Final Office Action dated Aug. 29, 2008, 5 pages; and response dated Dec. 29, 2008, 7 pages.

In the US Patent and Trademark Office U.S. Appl. No. 11/206,590, Final Office Action dated Apr. 15, 2009, 6 pages; and response dated Jun. 15, 2009, 9 pages.

In the US Patent and Trademark Office U.S. Appl. No. 11/206,590, Advisory Action dated Jul. 13, 2009, 3 pages; and response dated Sep. 14, 2009, including Request for Continued Examination.

In the US Patent and Trademark Office U.S. Appl. No. 11/206,590, Non-Final Office Action dated Sep. 29, 2009, 7 pages; and response dated Nov. 11, 2009, 8 pages.

In the US Patent and Trademark Office U.S. Appl. No. 11/206,590, Final Office Action dated Feb. 3, 2010, 7 pages.

In the US Patent and Trademark Office U.S. Appl. No. 11/206,893, Non-Final Office Action dated Feb. 18, 2009, 7 pages; and response dated May 18, 2009, 7 pages.

In the US Patent and Trademark Office U.S. Appl. No. 11/207,121, Non-Final Office Action dated Feb. 13, 2008, 11 pages; and response dated Mar. 14, 2008, 12 pages.

In the US Patent and Trademark Office U.S. Appl. No. 11/207,121, Non-Final Office Action dated Jun. 20, 2008, 14 pages; and response dated Sep. 22, 2008, 13 pages.

In the US Patent and Trademark Office U.S. Appl. No. 11/207,121, Final Office Action dated Dec. 24, 2008, 16 pages; and response dated Mar. 20, 2009, 12 pages, including Request for Continued Examination.

In the US Patent and Trademark Office U.S. Appl. No. 11/207,121, Non-Final Office Action dated Apr. 27, 2009, 17 pages; and response dated Jul. 27, 2009, 11 pages.

In the US Patent and Trademark Office U.S. Appl. No. 11/207,121, Final Office Action dated Nov. 27, 2009, 16 pages; and response dated Feb. 26, 2010, 13 pages, including Request for Continued Examination.

Feng et al.; "Adsorption of High Density Lipoproteins (HDL) on Solid Surfaces"; Journal of Colloid and Interface Science; 1996; vol. 177; pp. 364-371.

Nauck et al.; "Methods of measurement of LDL-cholesterol: a critical assessment of direct measurement by homogeneous assays versus calculation"; Clinical Chemistry; 2002; vol. 48, No. 2; pp. 236-254.

Santee; "Accuracy and precision of the Cholestech LDX System in monitoring blood lipid levels"; American Journal of Health-System Pharmacy; 2002; vol. 59; pp. 1774-1779.

Sigiuchi et al.; "Direct Measurement of High-Density Lipoprotein Cholesterol in Serum with Polyethylene Glycol-Modified Enzymes and Sulfated α-Cyclodextrin"; Clinical Chemistry; 1995; vol. 41, No. 5; pp. 717-723.

Warnick et al.; "Evolution methods for measurement of HDL-cholesterol: from ultracentrifugation to homogeneous assays"; Clinical Chemistry; 2001; vol. 47, No. 9; pp. 1579-1596.

* cited by examiner

APPARATUS AND METHOD OF MANUFACTURING BODILY FLUID TEST STRIP

CROSS-REFERENCE TO RELATED APPLICATIONS

This application is a divisional of U.S. application Ser. No. 11/206,590 filed Aug. 17, 2005, which claims the benefit of U.S. Provisional Application No. 60/602,210 filed Aug. 17, 2004, which applications are hereby incorporated by reference to the same extent as though fully contained herein.

BACKGROUND OF THE INVENTION

1. Field of the Invention

The invention in general relates to disposable dry test strips for testing bodily fluids, and more particularly to a method and apparatus for manufacturing such test strips.

2. Statement of the Problem

The level of certain analytes in blood and other body fluids is often used to diagnose disease, determine disease risk factors, monitor the course of a therapy, or determine the presence of illicit drugs. In recent years, analytes carried in blood have been evaluated to determine various cholesterol and triglyceride levels as a significant indicator of risk of coronary heart disease. Physicians commonly order what is referred to in the art as a "full lipid panel" for patients to determine the concentration of total cholesterol, high-density lipoprotein cholesterol (HDL), low-density lipoprotein cholesterol (LDL), and triglycerides.

The blood analysis necessary to determine bodily fluid analytes, such as cholesterols, may be performed in a clinical setting in a laboratory or on site using dry test strips. In the laboratory, the blood is centrifuged to separate the red blood cells from the plasma, and carefully controlled chemical tests in test tubes are performed to determine the concentration of analytes. Dry test strips utilize several membrane layers to separate red blood cells from blood plasma, react the plasma with a particular reagent or reagents, and obtain a signal indicative of the concentration of a particular analyte. See, for example, U.S. Pat. No. 4,774,192 issued Sep. 27, 1988 to Terminiello et al.; U.S. Pat. No. 4,477,575 issued Oct. 16, 1984 to Peter Vogel et al.; U.S. Pat. No. 5,135,716 issued Aug. 4, 1992 to Tatin B. Thakore; U.S. Pat. No. 5,597,532 issued Jan. 28, 1997 to James Connolly; U.S. Pat. No. 6,171,849 issued Jan. 9, 2001 to Walter Rittersdorf et al.; U.S. Pat. No. 6,759,190 issued Jul. 6, 2004 to Jinn-Nan Lin et al.; United States Patent Application Publication No. US2004/0126830 published Jul. 1, 2004 on an invention of Bruce Shull et al.; and United States Patent Application Publication No. US2005/0003523 published Jan. 6, 2005 on an invention of Sunil Anaokar et al.

FIG. 1 illustrates the conventional manufacturing process of a dry test strip. Test holder assembly 100 includes a plurality of test strip holders 101, 102, 103, 104, and 105. FIG. 1 also shows a roll 110 of test membrane strip 112, which has been partially unrolled across holder assembly 100. As is known in the art, the test membrane strip 112 is a multilayered structure, the layers of which have been previously impregnated with the chemicals required for the test. An element of the test membrane strip 112 is cut away to show the sensor port 136 of holder 104. The holders 103-105 are joined together along score lines, such as 108. A typical holder 104 includes a main body portion 120 and a cover portion 122. The cover portion of each holder, such as 104, is folded at the line 129 between cutouts 127 and 128 so that holes, such as 124, snap onto posts, such as 126, to lock the membrane 112 in place with sample port 145 located directly above sensor port 136. The individual holders 101, 102, etc., then are cut apart at score lines, such as 108. The cutting process also cuts the test strip 112 into rectangles, such as 117, between the dotted lines at each side of holder 102, each rectangle of test strip being held between the cover, such as 122, and body, such as 120, of the corresponding test holder. The completed holder, such as 102, with its corresponding test strip rectangle, such as 117, held in place makes a completed individual dry test assembly 129. While only five holders are shown in the manufacturing assembly 100 of FIG. 1, generally there are many more holders in a manufacturing assembly, which is illustrated by the dashed lines 106 and 107 in FIG. 1

The above-described manufacturing process permits a semi-automated manufacturing process, in that a roll 110 of membrane can be applied across a large number of holders in a single process, and the process of separating the holders 101, 102, etc., also cuts the membrane into separate test elements while the individual test elements, such as 117, are trapped between the cover, such as 142, and main body, such as 140. However, as will be shown in detail below, this manufacturing process also contributes significantly to the inaccuracy of the prior art test strip.

Dry test strips have the advantage that relatively unskilled people at the site where the test is ordered or needed can perform them in a few minutes. However, since the chemistry required to perform the test is in place in the strip, it cannot easily be varied depending on the particular sample to be tested, and the user may not always apply the same amount of bodily fluid via the sample port 145. This results in an inherent inaccuracy of the conventional dry test strip measurement as compared to a clinical process performed in the laboratory, where the bodily fluid and chemicals can be more carefully measured. Further, since the strips are mass produced, they are subject to manufacturing variations that are determined by the manufacturing process. Thus, dry test strips, while very convenient, are more inaccurate than clinical analyses, and their usefulness is limited to situations in which high accuracy is not required. If the inaccuracies due to manufacturing variations could be reduced significantly, a much more useful test strip would result.

SUMMARY OF THE INVENTION

The present invention overcomes the above and other problems by providing a manufacturing process and manufacturing apparati in which the chemical and other variables within a test strip can be more easily controlled, thus resulting in a more accurate test strip.

One way the invention improves the accuracy of the test strip can be understood by referring to FIG. 2, which shows a prior art test strip 112. Superimposed on the test strip 112 are dashed circles 201, 202, 203, 204, 205, and 206 which show the areas of the test strip that are actually used in a test. That is, the areas 201, 202, etc., correspond to the areas that are directly above each of the sensor ports, such as 136, in each of the holders, 101, 102, etc., of FIG. 1. It is evident from FIG. 2 that a lot of the test strip is wasted. That is, the area spanning the distance 213 between two of the actually used areas is not used. Also, the area 214 above the actually used areas and the area 215 below the actually used areas is also wasted. However, this waste is not the principle problem with the prior art manufacturing process.

The bigger problem is that the space 213 between adjacent used areas greatly increases the distance between the first used area and the last used area on a roll of test strip. The individual layers of a test strip ribbon are impregnated with the test chemicals by drawing the test strip ribbon through a bath, drying it, and then rolling it for use in the manufacturing process of FIG. 1. Since the rolls 110 are very long, the concentration of chemicals in the bath changes from the first used area to the last, and thus the chemical content of the test strip layer will change also. This discrepancy between the chemical content for areas near the beginning of the test strip roll 110 and areas near the end of the test strip roll 110 results in a manufacturing variation giving rise to inaccuracies in testing with the dry test strip.

The invention provides a manufacturing process in which the test strip elements used in each test strip holder are individually cut from the test strip ribbon. Preferably, the size of the element cut is determined by the size of the sensor port or sample port rather than the width of the test strip holder.

The invention provides a method of manufacturing a dry test strip for determining a characteristic of a bodily fluid, the method comprising: providing a dry test strip holder having a sensor port; providing a sheet or ribbon of test strip material; cutting a test element from the test strip material; and thereafter applying the test element to the dry test strip holder in a location covering the sensor port. Preferably, the cutting comprises engaging the sheet or ribbon with a die. Preferably, the cutting comprises: providing a die and a punch; locating the sheet or ribbon between the die and the punch; and driving the punch against the sheet or ribbon and into the die. Preferably, the providing comprises providing the die having a channel through it, and the applying comprises: locating the die above the strip holder with the channel above the sensor port; and using the punch to push the cut test element through and out of the die channel. Preferably, the dry test strip holder includes a test element well located above the sensor port and a flexible retainer encircling the test element well; the providing further comprises providing an inserter having a ramped surface, the ramped surface located about the periphery of the channel; and the applying further comprises pressing the ramped surface of the inserter against the retainer to bend it in a direction away from the sensor port and inserting the cut test element into the well. Preferably, the method further engages the retainer with a cap to capture the cut test element in the well. Preferably, the test holder further includes a test element well located above the sensor port, and the applying comprises placing the cut test element in the test element well. Preferably, the dry test strip holder further includes a cap, and the method further comprises capping the test element well with the cap. Preferably, the cutting comprises cutting a circular test element. Alternatively, the cutting comprises cutting a rectangular test element. Preferably, the providing a dry test strip holder comprises providing a dry test strip holder having a sensor port, the sensor port having a maximum dimension, and the cutting comprises cutting a test element having a maximum dimension that is 50% or less of the sensor port maximum dimension. More preferably, the cutting comprises cutting a test element having a maximum dimension that is 75% or more of the width of the sheet or ribbon; most preferably, the cutting comprises cutting a test element having a maximum dimension that is 90% or more of the width of the sheet or ribbon.

The invention also provides a method of manufacturing a dry test strip for determining a characteristic of a bodily fluid, the method comprising: providing a dry test strip holder having a sensor port; the sensor port having a maximum dimension; providing a sheet or ribbon of test strip material; cutting a test element from the test strip material, the test element having a maximum dimension that is 50% or less larger than the sensor port maximum dimension; and applying the test element to the dry test strip holder in a location covering the sensor port. Preferably, the cutting comprises cutting a test element having a maximum dimension that is 30% or less larger than the sensor port maximum dimension. More preferably, the cutting comprises cutting a test element having a maximum dimension that is 15% or less larger than the sensor port maximum dimension.

The invention further provides a machine for manufacturing a dry test strip, the machine comprising: a die having a cutting edge substantially shaped in the form of the outer perimeter of a dry test strip element and a channel extending away from the cutting edge; a punch shaped to snugly and slidably fit in the channel; and a support for holding a sheet or ribbon of dry test material between the punch and the die. Preferably, the machine further comprises an inserter having a ramped surface formed about the periphery of the channel and extending away from the distal end of the channel. Preferably, the inserter is cone-shaped. Preferably, the machine further comprises a dry test strip material drive for moving the sheet or ribbon between the punch and the die.

The invention not only provides a more accurate test strip, but also reduces waste of impregnated membrane. Further, the invention provides a more efficient manufacturing process. These and other objects and benefits of the invention will become apparent from the following written description and accompanying figures.

DETAILED DESCRIPTION OF THE PREFERRED EMBODIMENT

Figure 1:
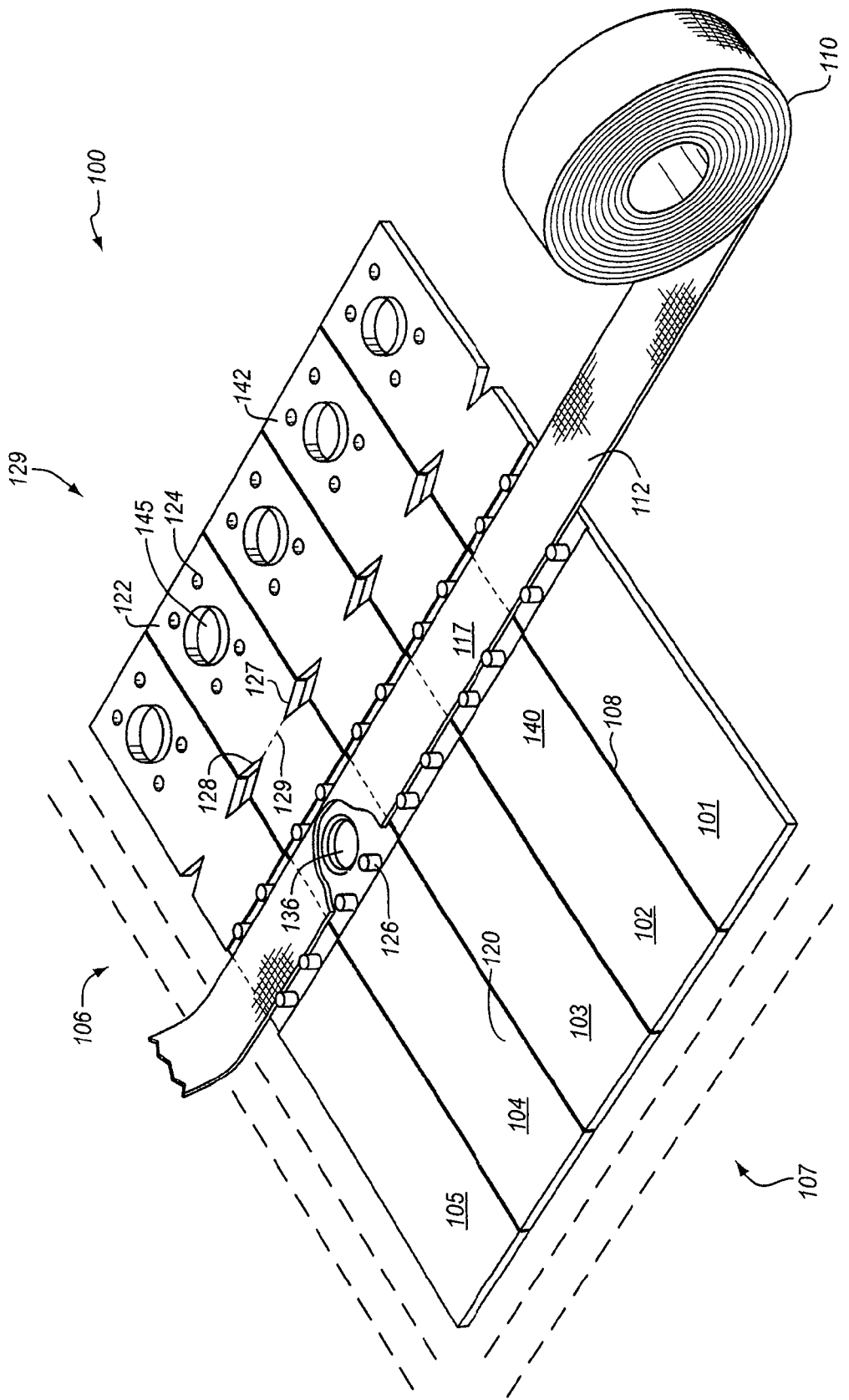
FIG. 1 illustrates a conventional manufacturing process of dry test strips in the prior art using a roll of fabricated test membrane ribbon.

For the purposes of promoting an understanding of the principles of the invention, reference will now be made to the embodiments illustrated in the drawings and described in the following. It is understood that no limitation to the scope of the invention is thereby intended. It is further understood that the present invention includes any alterations and modifications to the illustrated embodiments and includes further applications of the principles of the invention as would normally occur to one skilled in the art to which this invention pertains. It should also be understood that, in accordance with the patent law, the drawings are not intended to be precise engineering drawings of the invention, but rather are only intended to illustrate the invention. For example, the scale of the drawings and relative size of the various parts are generally altered so as to better illustrate the invention within the constraints of a written document such as this.

The dry test strip manufacturing process according to the invention involves three distinct inventive aspects. The first aspect is a novel method of dividing up a test strip ribbon during the manufacturing process in a manner that is not dictated by the size of the test strip holder, with as little wasted ribbon as possible. This aspect is illustrated in FIGS. 3-6. The second aspect is a test strip holder which permits secure individual placement of the test strip elements cut from the ribbon. One example of this holder 20 is shown in FIGS. 8-14. In this aspect, the individual test strip elements 50 (FIG. 8) are placed in a test strip element well 64 in the holder 20, and a cap 40 is snapped on to trap the test strip element 50 between a cap flange 44 and a test strip element support 69 (FIG. 14). The third aspect is the machinery and process of cutting the test strip elements 50 from the ribbon and inserting them in the test strip element well 64 of the test strip holder, which aspect is illustrated in FIG. 15. As will be seen below, although the invention is best understood by describing the combination of these three aspects, each of these aspects of the invention are separately useful.

Figure 3:
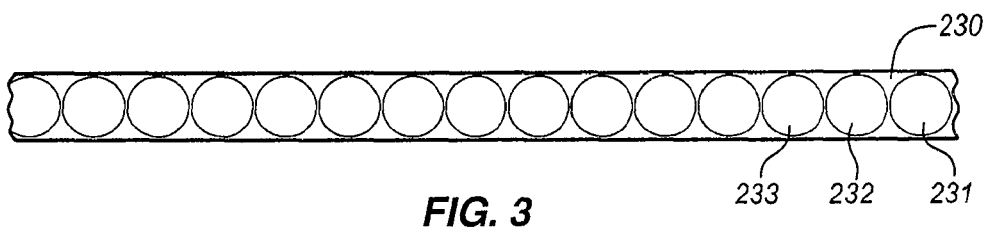
FIGS. 3-6 illustrate various exemplary methods according to the invention of apportioning a test membrane ribbon.

FIG. 3 illustrates a test strip ribbon 230 according to the invention showing test strip elements 231, 232, 233, etc., that, according to the invention, are each individually cut from the test strip ribbon. As can be seen from FIG. 3, each individual test strip element, such as 232, is cut from an area of the ribbon that is substantially adjacent the area from which the neighboring test strip elements, such as 231 and 233, are cut. This significantly reduces the wasted area between test strip elements, and thus significantly reduces the length of the test strip ribbon required for a given number of dry test strip assembles. In addition, since the elements 231, 232, 233, etc., are individually cut, the cut out area can extend across substantially the full width of the test strip ribbon 230, thus further reducing waste.

Figure 4:
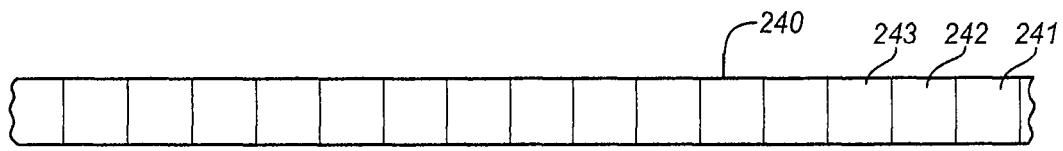

While circular test strip elements 231, 232, 233, etc., are preferred for reasons discussed below, the test strip elements can be cut into any desired shape. FIG. 4 illustrates how a strip 240 may be cut into rectangular, preferably square, elements 241, 242, 243, etc., each of which is of a diameter approximately the diameter of a sensor port 136. As will be seen in more detail below, each element 231, 232, 233, etc., is much smaller than the test strip elements, such as 117 in FIG. 1, being substantially the size of a test strip well, such as 64 (FIG. 10), though the test strip well for these test strip elements will be square instead of circular like well 64.

Figure 5:
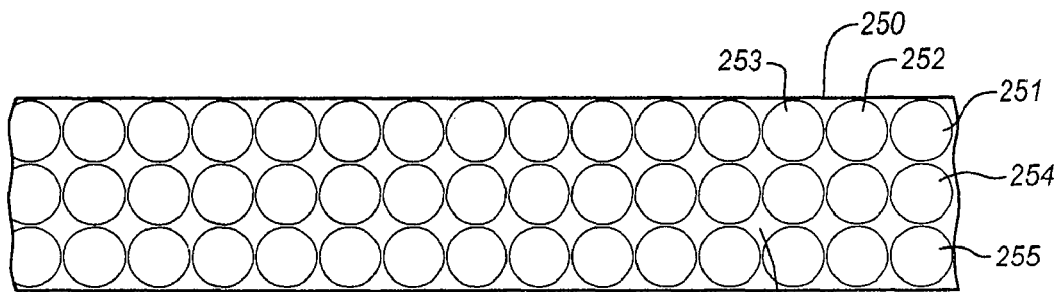
Figure 6:
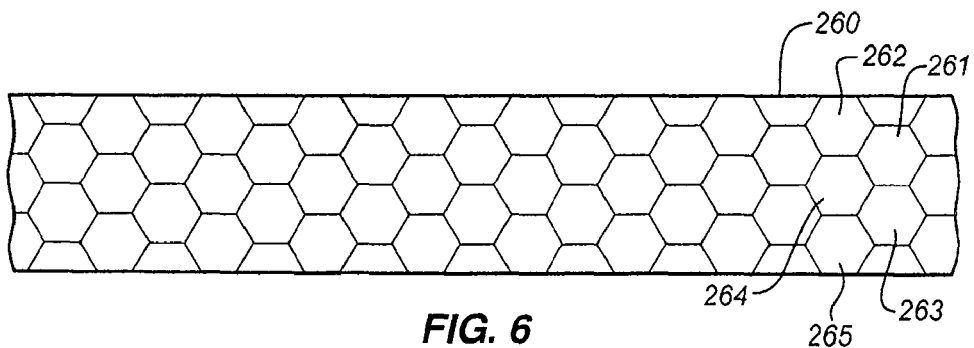
Figure 7:
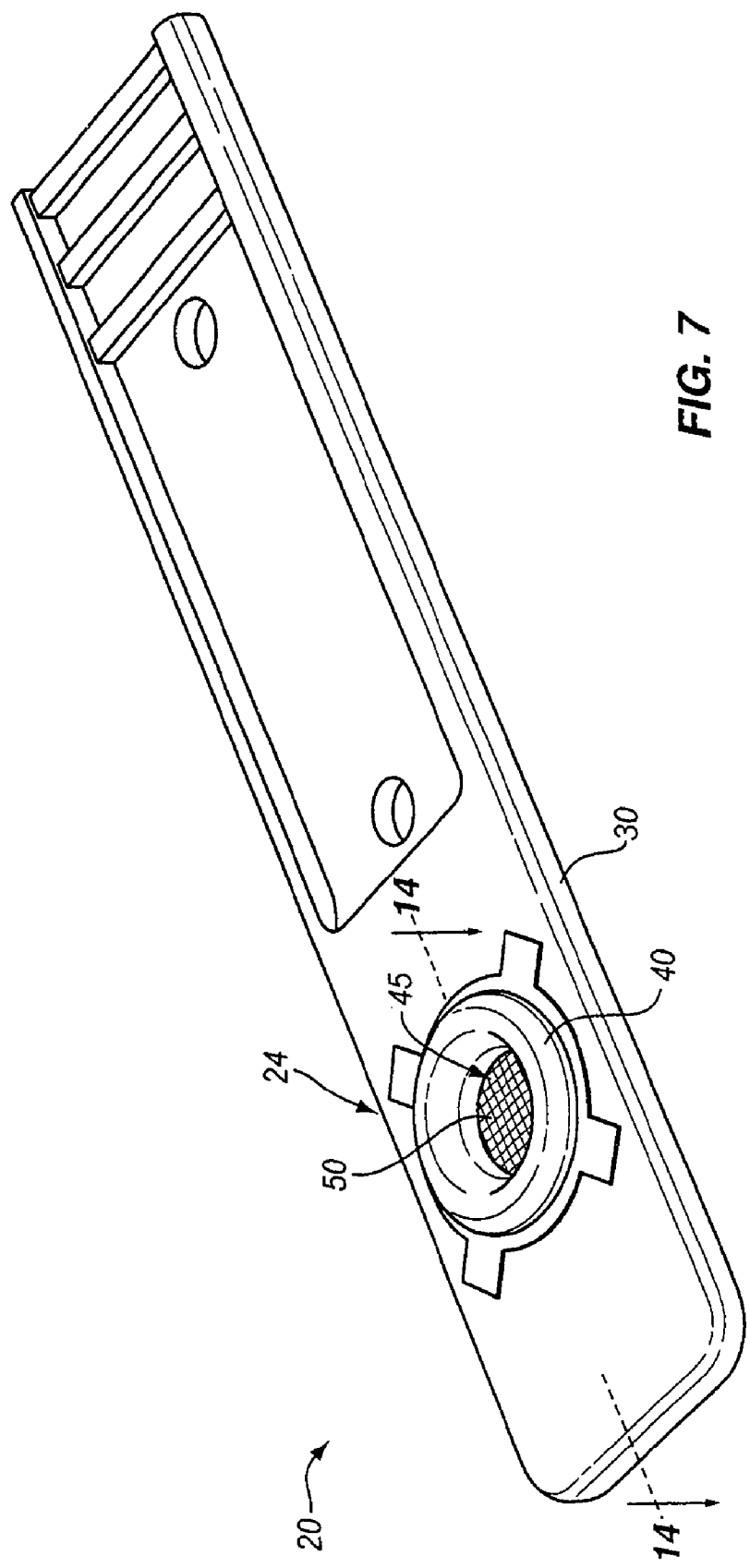
FIG. 7 is a perspective view of a preferred embodiment of a test strip assembly according to the invention.

FIG. 5 illustrates an alternative embodiment of a test strip sheet 250 from which test strip elements such as 251, 252, 253, 254, 255, etc., may be cut. In FIG. 5, the sheet is approximately the width of three test strip elements. Each test strip element 251, 252, etc., is substantially adjacent the neighboring test strip elements. FIG. 6 illustrates a variation of the test sheet of FIG. 5, in which the individual test strip elements 261, 262, 263, 264, 265, etc., are made hexagonal and are staggered to fill in the unused areas, such as 258, that occurs between the test strip elements in the embodiment of FIG. 5. Those skilled in the art will recognize that many other test strip ribbons or sheets having different patterns of test strip elements may be used. The key aspects that FIGS. 3-6 are intended to illustrate are that the test strip elements are individually cut from the ribbon or sheet, and the cuts are designed so that the amount of test strip ribbon or sheet that is used is maximized.

Figure 2:
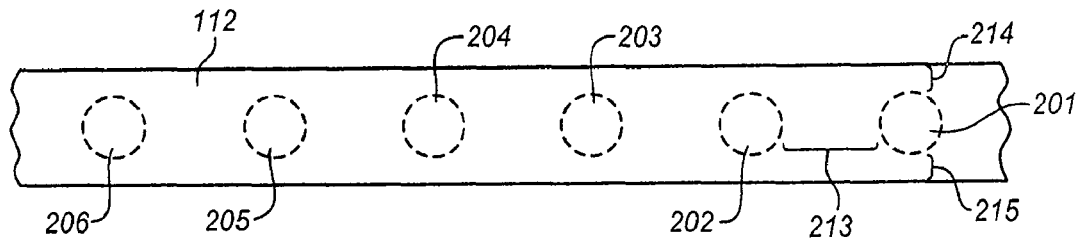
FIG. 2 illustrates the area of a prior art membrane ribbon which is actually used in the blood analysis processes of the prior art.
Figure 8:
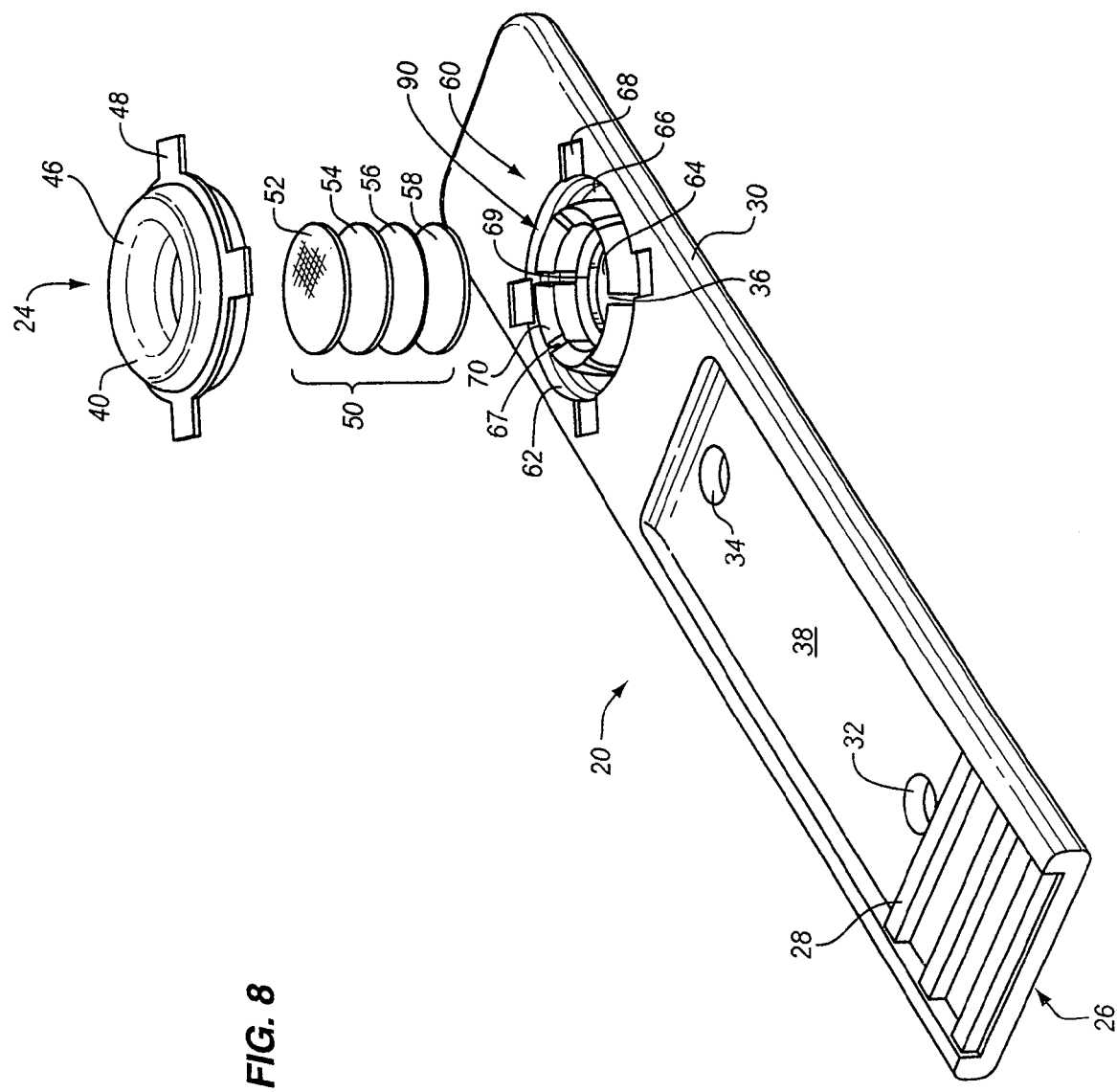
FIG. 8 is an exploded perspective view of the test strip assembly of FIG. 7.

An assembled dry test strip assembly 20 is shown in FIG. 2 and an exploded perspective view of the test strip assembly 20 is shown in FIG. 8. Test strip assembly 20 includes a preferably elongated test strip holder body 30, a test strip element 50, which is visible through sample port 45 in FIG. 2, and a test strip holder structure 24. Test strip holder structure 24 includes a holder base element 60 (FIG. 3) and a holder cap 40. Carrier body 30 includes a grip portion 26, openings 32 and 34, sensor port or test opening 36, and holder base 60. Grip portion 26 includes raised ribs 28, which permit the test strip user to easily grip the carrier body 30 with his or her fingers.

Figure 9:
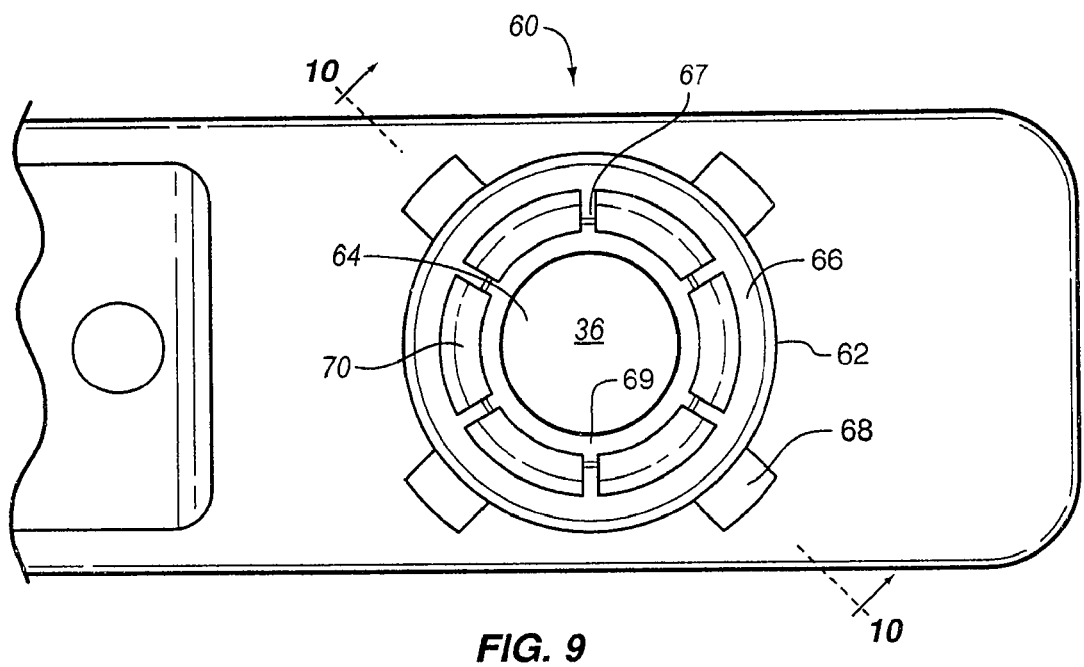
FIG. 9 is a top view of a portion of the base portion of the test strip assembly of FIG. 7.
Figure 10:
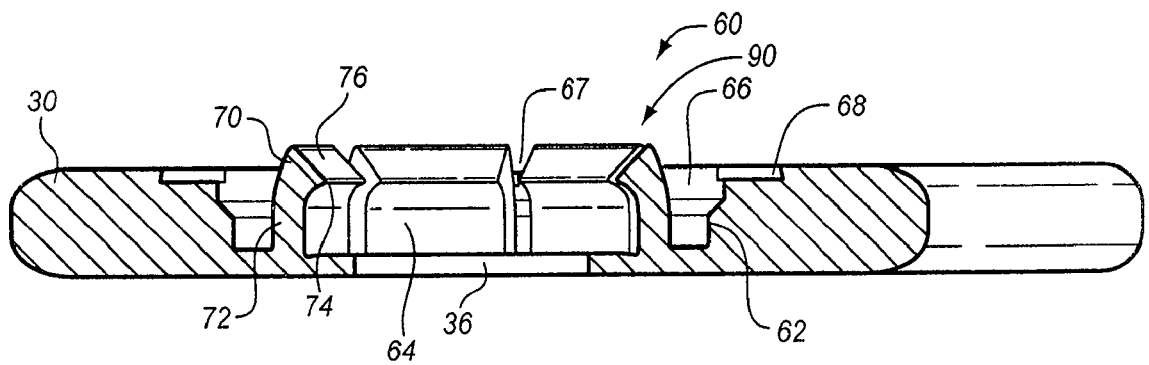
FIG. 10 is a cross-sectional view of the base portion of the test strip assembly of FIG. 7 taken through the line 10-10 of FIG. 9.

The holder base 60 is shown in FIGS. 8, 9, 10, and 14. FIG. 8 shows a perspective view, FIG. 9 shows a top view, FIG. 10 shows a cross-sectional view through lines 5-5 in FIG. 9, and FIG. 14 shows the cap 40 in place over holder base 60. Preferably, holder base 60 includes a well 62 formed in body 30, alignment recesses 68, and retainer 90, which is preferably flexible. Well 62 has an upward sloping well wall 83 completely encircling the test opening (sensor port) 36. Retainer 90 preferably comprises fingers 70 and separates well 62 into an inner portion 64 which forms a test strip well 62 and an outer portion 66, which is preferably relatively small in volume, being just big enough to allow fingers 70 to flex. Well 62 and retainer 90 encircle the test strip sensor port 36. In this disclosure, the term "encircle" does not necessarily mean the encircling structure forms a circle, but rather it has the broader common meaning of "to pass completely around". In the preferred embodiment, however, the well 62 and retainer 90 do form a circle. In the preferred embodiment, there are four alignment recesses 68 and six fingers 70, though the invention contemplates that any number suitable to perform the functions described below may be used. Each finger 70 includes a stem portion 72, a hook portion 74, and a ramp portion 76 that is preferably formed at an acute angle to a vertical line perpendicular to the plane of body 30. Fingers 70 are separated by channels 67. The bottom of well 62 forms a test strip support 69 around port 36 on which, as will be seen below, the test strip element 50 rests, as best shown in FIG. 9.

Figure 11:
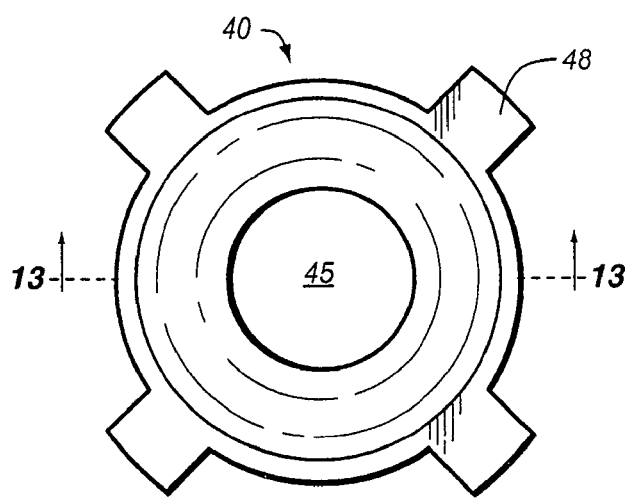
FIG. 11 is a top plan view of the cap portion of the test strip assembly of FIG. 7.
Figure 12:
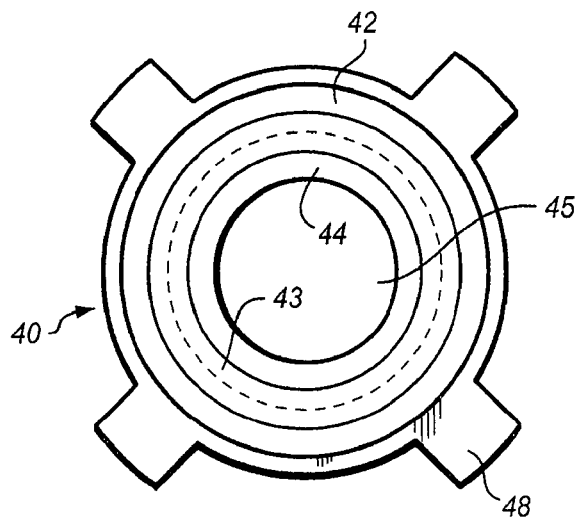
FIG. 12 is a bottom plan view of the cap portion of the test strip assembly of FIG. 7.
Figure 13:
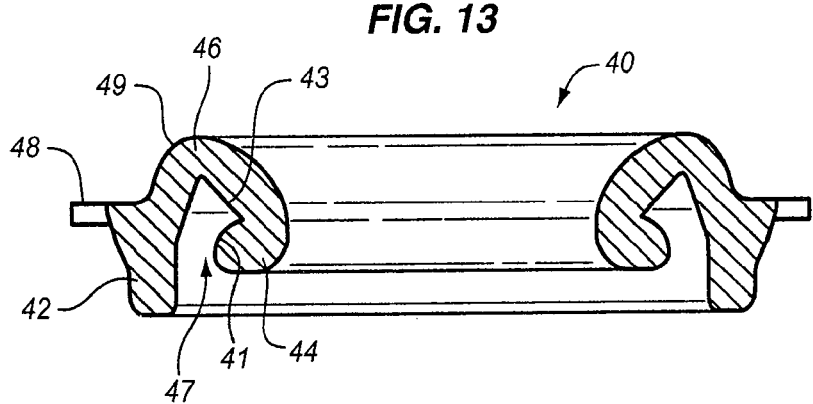
FIG. 13 is a cross-sectional view of the cap of FIG. 11 taken through the line 13-13 of FIG. 11.
Figure 14:
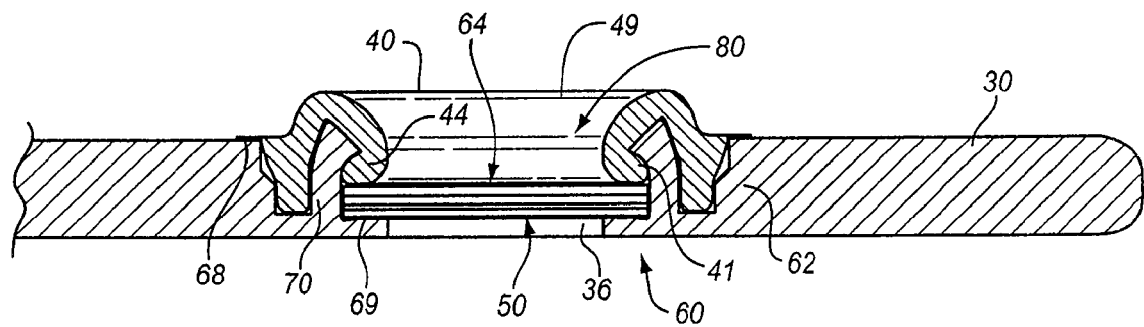
FIG. 14 is cross-sectional view of the assembled test strip assembly of FIG. 7 taken through the line 14-14 of FIG. 7.
Figure 15:
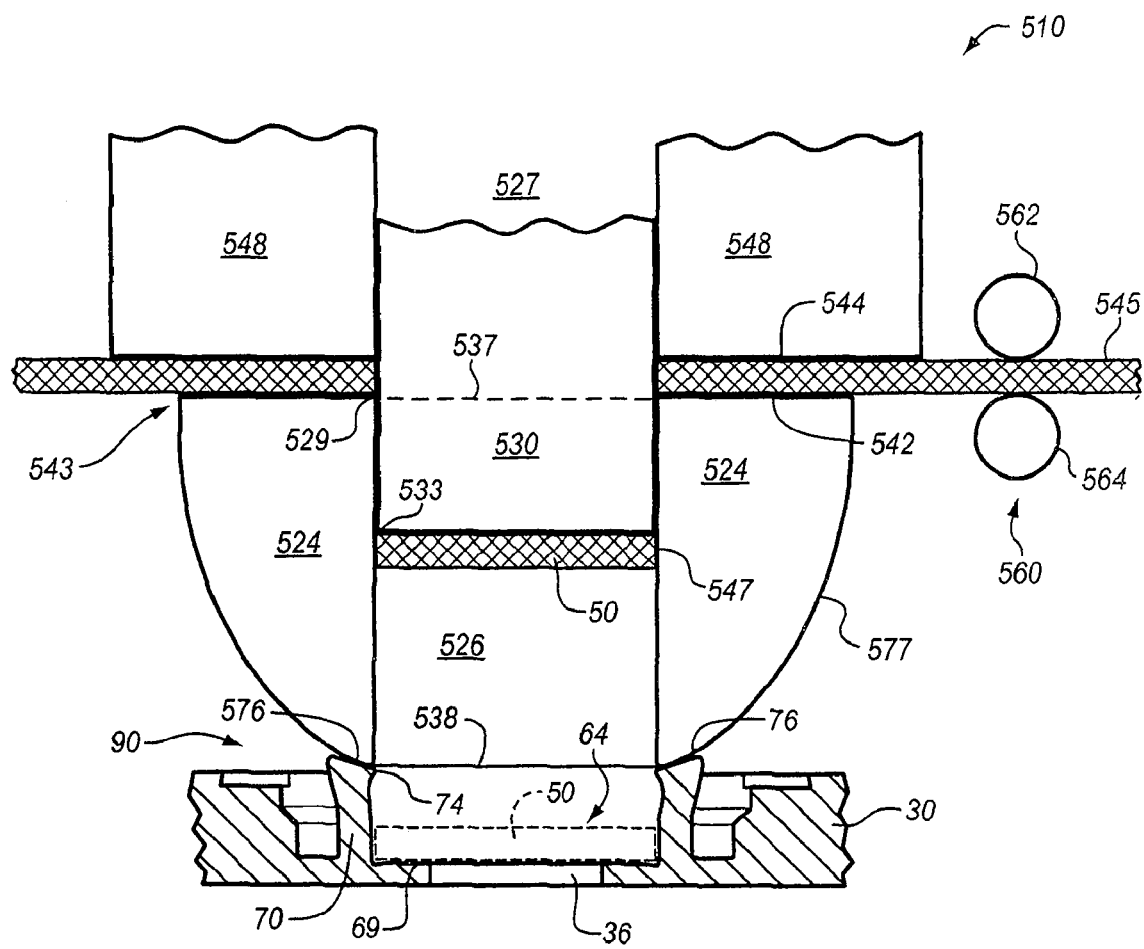
FIG. 15 is a plan view illustrating an exemplary manufacturing process and manufacturing apparatus according to the invention.

Cap 40 is shown in FIGS. 8 and 11-14. FIG. 8 shows a perspective view, FIG. 11 shows a top plane view, FIG. 12 shows a bottom plane view, FIG. 13 shows a cross-sectional view through line 13-13 of FIG. 11, and FIG. 14 shows a cross-sectional view of the cap 40 in place over the holder base 60. Cap 40 includes an outer foot 42, an inner flange 44, and a connecting portion 46, which, as will be seen below, forms the brim 49 of a bodily fluid container 80. The outer foot 42 and inner flange 44 have different lengths, with the inner flange being shorter. The difference in lengths is less than the thickness of test strip element 50, so that the inner flange 44 and test strip support 69 engage strip element 50 sufficiently to secure it in place. Preferably, the difference is sufficient so that flange 44 and test strip support 69 compress strip element 50 between them. The bottom 43 of connecting portion 46 is shaped to form a groove 47 into which fingers 70 fit snuggly. A lip 41 is formed on flange 44 (FIGS. 8 and 9) which engages hook 72 to latch cap 40 on holder base 60. The distal end 84 of flange 44 is smooth and rounded so as not to damage test strip element 50.

Test strip element 50 is shown in FIGS. 8 and 14 and is preferably formed of a plurality of layers. Each layer performs a specific function as required by each specific test. In the preferred embodiment, there is a "spreading" layer 52 to ensure even distribution of the whole blood sample, a "separation" layer 56 to obtain a clarified plasma/serum sample, a layer or layers 54 to hold specific test reagents in sequence as needed by each specific assay, and a final "color" or "test reaction" layer 59 to provide a matrix on which a specific color or test reaction will develop for each specific test. The order of the layers can vary. For example, the separation layer may come before or after the reagent layer(s). The details of the test strip chemistry are not pertinent to the present invention, and therefore will not be described in detail herein. Those skilled in the art will understand that this chemistry can take many different forms, depending on the bodily fluid to be analyzed, such as blood or urine, and the analyte, such as total cholesterol, ketones, HDL, LDL, triglycerides, sugars, etc., that is to be characterized.

The test assembly 20 is assembled as shown in FIGS. 8 and 15. The test element cutting and insertion system 510 is shown in FIG. 15. Cutting and insertion system 510 includes a die/inserter 524, a punch 530, a punch guide 548, and a test strip material drive mechanism 560. A sheet or ribbon 545 of test strip material is also shown in FIG. 15. The sheet or ribbon 545 of test strip material is preferably multilayered as shown at 50 in FIG. 8. The die/inserter 524 has channel 526 passing through the die, a cutting edge 529 formed about the perimeter of the proximal end 537 of the channel, and a ramped surface 576 about the periphery of the distal end 538 of the channel. The cutting edge 529 is substantially shaped in the form of the desired outer perimeter 547 of a test element 50. The upper surface 542 of die/inserter 524 is preferably flat and provides a support and guide for test sheet or ribbon 545. Preferably, the outer surface 577 of the die/inserter is cone-shaped. Test sheet or ribbon drive mechanism 560 preferably comprises a first roller 562 and a second roller 564 that rotate in opposite directions to move sheet or ribbon through guide slot 543. Punch guide 548 includes a bore 527 in which the punch slides. The lower surface 544 of guide 548 is preferably flat and forms the upper guide for test sheet or ribbon 545. Punch 530 is sized and shaped to slide snuggly in channel 526. The punch 530 has a cutting edge 533 formed about the perimeter of punch 530.

The manufacturing process is as follows. Cutting and inserting assembly 510 is located above the test port 36 in test strip holder body 30, preferably by moving an injection molded test holder assembly having a plurality of test strip holder bodies 30 into place below the inserter and under the distal end 538 of die/inserter 524. However, this could also be done by moving the cutting and inserting assembly 510. Punch 530 is driven downward into contact with sheet or ribbon 545. Punch edge 533 cooperates with the die edge 529 to cut out a test element 50. Punch 530 continues to be driven downward, pushing test element 50 through die channel 526 and out its distal end 538. Meanwhile, cone-shaped inserter 524 is driven downward so that ramp surface 576 presses against the ramps 76 of the fingers 70 and spreads them sufficiently to drop the assembled test strip element 50 onto test strip support 69. The punch and die/inserter 524 then retreat upward, and holder body 30 moves to a different assembly station where cap 40 is then pressed home on retainer 90, with fingers 70 forced into groove 47, compressing test strip element 50 sufficiently to hold it in place.

The carrier body 30, holder base 60, and cap or cover 40 are preferably made of plastic or other suitable material. The preferred plastics are polypropylene or nylon, though other plastics may be used. Preferably, the plastic parts are injection molded, and cap 40 is sonic welded to holder base 60 at locator tabs 68. Thus, the placement tabs enable the cap to be welded without contact with the main body of cap 60. Preferably, the plastic parts, particularly the cap 40, are color-coded to correspond to the particular test, such as HDL, LDL, total cholesterol, etc., for which the test strip element, such as 50, is designed.

The test strip operates generally as follows. A drop of bodily fluid, such as blood, is placed within the sample application port 45 of cap 40. It is evenly dispersed across the opening by test strip layer 52 and percolates vertically downward. The membrane 54 separates the unwanted material, such as the red blood cells, from the rest of the fluid, such as the serum. The red blood cell filtration/reagent membrane 56 includes reagents that react with undesired analytes that would compromise the test in membrane 58. The desired analyte preferably reacts in membrane 58 to produce a color.

A feature of the invention is that the test strip element, such as 50, preferably does not include any glue, adhesive, or other substance to hold it in place. Such substances can get into the test sample and compromise the test to make it less accurate and reliable.

The methodology of the invention is a self-consistent and self-reinforcing process. The materials and processes of the invention are carefully engineered so that more accurate and more reliable results can be achieved with more economical test strip assembly. The much smaller sized test strip element results in less test strip material being used. In addition, the smaller sized test element keeps the bodily fluid confined to a smaller test area, which prevents leaching out of bodily fluid away from the observation port, which reduces test accuracy. That is, the bodily fluid, such as blood plasma, is more focused into the observation area permitting better test control.

The invention also more readily lends itself to disc-shaped test elements 50. Blood or other bodily fluids naturally form a circular drop, which when deposited on the test element, naturally spreads in a circular form. Thus, a disc-shaped test element 50 lends itself to more uniform distribution of the bodily fluid over the element, which, in turn leads to more accurate results.

The preferred test strip according to the invention is intended to be used in a photometric device such as that described in U.S. Pat. No. 5,597,532, which is hereby incorporated by reference to the same extent as though fully disclosed herein. The structure and operation of this device is well known in the art and thus will not be described in detail herein. Further, any device that has the ability to determine the intensity of light, the frequency or wavelength of light, or other property of light reflecting, scattering, or otherwise interacting with a dry test strip, may be used to read the test strip of the invention.

While the invention has been illustrated and described in detail in the drawings and foregoing description, the same should be considered as illustrative and not restrictive in character. It is understood that only the preferred embodiments have been presented and that all changes, modifications, and further applications that come within the spirit of the invention are desired to be protected, For instance, while the illustrative embodiments only show a single sample application port and a single corresponding sensor port, multiple sample ports and multiple sensor ports are contemplated. Although the invention has been explained in terms of test elements that produce a color when reacted with a bodily fluid and which are read with a photometer, other types of test elements, such as test elements that react to provide other optical characteristics or to provide an electrical characteristic change that can be read with an electronics instrument, can also be used.

There has been described a novel invitro, dry test strip system that is useful to assay bodily fluids for a variety of analytes. It should be understood that the particular embodiments shown in the drawings and described within this specification are for purposes of example and should not be construed to limit the invention, which will be described in the claims below. Further, it is evident that those skilled in the art may now make numerous uses and modifications of the specific embodiments described, without departing from the inventive concepts. For example, while the ports and test strips have been shown as circular, other shapes may also be used. Additional layers may be added to the test strip assembly. As a further example, cap 60 may be attached to a flap, such as described in U.S. Pat. No. 5,597,532, which would permit the cap 60 and body 30 to be made in a single piece in which the cap and body are connected. This has some advantages in parts management. It is also evident that the methods recited in many instances may be performed in a different order; or equivalent structures and processes may be substituted for the various structures and processes described. Consequently, the invention is to be construed as embracing each and every novel feature and novel combination of features present in and/or possessed by the bodily fluid analysis system herein described.

I claim:

1. A method of manufacturing a dry test strip for determining a characteristic of a bodily fluid, said method comprising:
    providing a dry test strip holder having a sensor port, said sensor port having a maximum dimension;
    providing a sheet or ribbon of test strip material;
    drawing said sheet or ribbon of test strip material through a reagent bath;
    cutting a test element from said test strip material, said test element having a maximum dimension that is 50% or less larger than said sensor port maximum dimension;
    applying said test element to said dry test strip holder in a location covering said sensor port; and
    engaging a cap with a test element well to hold said test strip element in the location, wherein said test element well is part of the dry test strip, wherein said cutting comprises:
    providing a die and a punch;
    locating said sheet or ribbon between said die and said punch; and
    driving said punch against said sheet or ribbon and into said die; and
    wherein said providing comprises providing said die having a channel through it, and said applying comprises:
    locating said die above said strip holder with said channel above said sensor port; and
    using said punch to push said cut test element through and out of said die channel.

2. The method of claim 1 wherein the test strips are capable of being used with a photometer through which reflectance is photometrically sensed through said sensor port to determine the characteristic of the bodily fluid.

3. A method as in claim 1 wherein:
    said test element well is located above said sensor port, and a flexible retainer encircles said test element well;
    said providing further comprises providing an inserter having a ramped surface, said ramped surface located about the periphery of said channel; and
    said applying further comprises pressing said ramped surface of said inserter against said retainer to bend it in a direction away from said sensor port, and inserting said cut test element into said well.

4. A method as in claim 3 wherein said inserter is cone-shaped.

5. A method as in claim 1 wherein said test holder further includes a test element well located above said sensor port, and said applying comprises placing said cut test element in said test element well.

6. A method as in claim 1 wherein said cutting comprises cutting a test element having a maximum dimension that is 75% or more of the width of said sheet or ribbon.

7. A method as in claim 1 wherein said cutting comprises cutting a test element having a maximum dimension that is 90% or more of the width of said sheet or ribbon.

8. A method as in claim 1 wherein no glue is used to hold said test element in said location.

9. A method as in claim 1 wherein said sensor port is configured to receive a photometric device.

10. A method as in claim 1 wherein said cap and said test element well hold said test strip element with a compressive force.

11. A method as in claim 10 wherein glue is not used to hold the test strip element.

12. A method as in claim 1 wherein the cutting and applying is performed by a single apparatus.

* * * * *